United States Patent
Kavey

(10) Patent No.: US 6,211,229 B1
(45) Date of Patent: Apr. 3, 2001

(54) TREATMENT OF TRANSIENT AND SHORT TERM INSOMNIA

(76) Inventor: Neil B. Kavey, 26 W. Orchard Rd., Chappaqua, NY (US) 10514

( * ) Notice: Subject to any disclaimer, the term of this patent is extended or adjusted under 35 U.S.C. 154(b) by 0 days.

(21) Appl. No.: 09/506,348

(22) Filed: Feb. 17, 2000

(51) Int. Cl.⁷ .................. A61K 31/335; A61K 31/55; A61K 31/35; A61K 31/495; A61K 31/13

(52) U.S. Cl. .................. 514/450; 514/217; 514/384; 514/252; 514/253; 514/255; 514/659; 514/453; 514/923

(58) Field of Search .................. 514/183, 923, 514/450, 659, 217, 384, 254, 253, 255, 453

(56) References Cited

U.S. PATENT DOCUMENTS 5,502,047 * 3/1996 Kavey .................. 514/183
5,643,897   7/1997 Kavey .................. 514/183

OTHER PUBLICATIONS

*Physician's Desk Reference*, 1999 ed., Medical Economics Company, Montvale NJ pp. 539–541 (trazadone).
*Physician's Desk Reference*, 2000 ed., Medical Economics Company, Montvale NJ pp. 3323–24 (trimipramine maleate).
*Physician's Desk Reference*, 2000 ed., Medical Economics Company, Montvale NJ pp. 549–551 (Amitriptyline HC1).
*Physician's Desk Reference*, 2000 ed., Medical Economics Company, Montvale NJ pp. 2366–67 (Doxepin HC1).

* cited by examiner

*Primary Examiner*—Theodore J. Criares

(57) ABSTRACT

The invention is directed to a method for the treatment of a patient suffering from transient or short term insomnia. The claimed method comprises the administration of a compound selected from the group consisting of the pharmaceutically acceptable forms of doxepin, amitriptyline, trimipramine, trazodone and mixtures thereof in dosages ranging from about 0.5 to about 20.0 milligrams.

31 Claims, No Drawings

TREATMENT OF TRANSIENT AND SHORT TERM INSOMNIA

FIELD OF INVENTION

This invention relates to a method for the treatment of individuals suffering from transient or short term insomnia.

BACKGROUND OF THE INVENTION

A large percentage of the adult population suffers from insomnia in some form at some time in their lives. This may vary from a single episode of one night's duration to chronic conditions. Transient insomnia is an insomnia that is present for one to several days, and is less than one week in duration. Short term insomnia is an insomnia of one to three weeks in duration. Chronic insomnia is typically accepted to involve episodes greater than three (3) weeks in duration. The insomnia may further involve onset insomnia (difficulty in falling asleep) and/or maintenance insomnia (difficulty in maintaining uninterrupted sleep). It is well known that the sleep deprivation resulting from such insomnia adversely affects cognition, safety and quality of life.

Known treatments for insomnia include the administration of medication, either of the non-barbiturate or barbiturate type, shortly before bedtime. While both types of sedatives may be used to effectively treat insomnia, neither is without its undesirable side effects. Barbiturate type sedatives, such as secobarbital (sold by Eli Lilly and Company under the tradename of Seconal®) are general depressants. While effective, these medications are well known to lose their effectiveness after a few days. Furthermore, they are highly addictive and commonly abused. They are therefore no longer widely prescribed.

The groups of medications now most commonly used for the treatment of insomnia are the imidazopyridines, the pyrazolopyrimidines and the benzodiazepines. There is one available hypnotic in the imidazopyridine group, one in the pyrazolopyrimidine group and there are five in the benzodiazepine group. They differ significantly in half lives but are otherwise very similar and equally effective. They have supplanted the barbiturates as the principal treatment for insomnia because they have less addiction potential and are associated with less risk for suicide than the barbiturates unless taken with alcohol. However, these groups, too, are addictive and their wide usage draws concern as their potential side effects become more apparent. These side effects include daytime sedation, decreased cognitive abilities such as memory loss and feelings of agitation after the drug's therapeutic effects pass.

In my prior inventions which issued as U.S. Pat. Nos. 5,502,047 and 5,643,897, I disclosed the novel use of low dose doxepin, amitriptyline, trimipramine, trazodone and mixtures thereof in the treatment of chronic insomnia. These medications are normally prescribed in high dosages for use as antidepressants (150–300 mg). All these medications have long half-lives, take several days to reach a steady state and take a minimum of 3–4 weeks to effect change in depressive affect. As such, those of ordinary skill in the art would expect that it would take a minimum of several days and as long as a month for such medications to effect a correction of an insomnia and thus their usefulness in chronic insomnia. A thorough study of my data, however, reveals the surprising fact that many patients benefited from the medications from day one of administration. That means that these medications, that have literally no effect on depression in the first days of administration, can, even at very low doses, have an immediate effect on insomnia, even before reaching steady state. This suggests an immediate mechanism of action that is entirely different from its action after weeks of accumulation, seemingly a direct neurochemical effect on sleep-wake mechanisms, an effect that is not at all obvious and, in fact, entirely unexpected considering the pharmacokinetics of the medications and their usefulness, to date, only in chronic conditions. With that recognition I have gone on to treat subjects with transient and short term insomnia and have discovered that very low doses of the stated medications (doxepin, amitriptyline, trimipramine, trazadone and mixtures thereof) can have an immediate beneficial effect on the sleep of subjects with transient and short term insomnia and are, therefore, useful agents for the treatment of individuals suffering from transient and short term insomnia of any etiology including the circadian desynchronization of jet lag.

OBJECTS OF THE INVENTION

It is an object of the present invention to develop a method for the successful treatment of transient and short term insomnia.

It is also an object of the present invention to develop a method for the successful treatment of insomnia other than chronic insomnia.

It is further an object of the present invention to develop a method for the successful treatment of insomnia associated with jet lag.

It is still another object of the present invention that the above methods involve the administration of non-addictive medications.

It is still a further object of the present invention to develop a method which does not involve the adverse effects associated with the current prescription hypnotics, i.e. residual sedation, lethargy, drowsiness, loss of cognitive ability and/or agitation.

SUMMARY OF THE INVENTION

The present invention is directed to a method for the treatment of a patient suffering from transient or short term (non-chronic) insomnia. The claimed method comprises administering to said patient a compound selected from the group consisting of the pharmaceutically acceptable forms of doxepin, amitriptyline, trimipramine, trazodone and mixtures thereof. The dosage for administration of doxepin, amitriptyline, trazodone, trimipramine and mixtures thereof ranges from about 0.5 to about 20.0 milligrams.

In one preferred embodiment of the present invention, the invention involves the administration to said patient doxepin, amitriptyline, trimipramine or mixtures thereof in a dosage of about 10 milligrams or less.

In another preferred embodiment of the present invention, the invention involves the administration to said patient trazodone in a dosage of about 15 milligrams or less.

DESCRIPTION OF THE INVENTION

The present invention is directed to a method for the treatment of a patient suffering from transient or short term (non-chronic) insomnia through the administration of very small doses of specific known psychotherapeutic agents. The claimed method may be used for the treatment of onset and/or maintenance insomnia.

The agents useful in the claimed invention include tricyclic compounds and a triazolopyridine derivative which are currently prescribed for the general treatment of depression. They are also prescribed for the treatment of the insomnia component of a depression in individuals suffering from depression. These compounds are known to possess a sedative effect in such individuals when administered in their normally-prescribed and available dosages (described below). The medications are now also being used in available dosages for the treatment of some subjects with insomnia. However, the use of these compounds at the extremely low dosages claimed herein for the successful treatment of transient or short term (non-chronic) insomnia in otherwise healthy individuals has not been reported and is not obvious in view thereof. For example, the compounds used in the present invention are currently prescribed for a 20–60 year old depressed patient population in dosages varying from about 75 to about 300 milligrams per day of the tricyclic compounds and about 150 to about 600 milligrams per day of the triazolopyridine compound. Further, the entire dosage of such medications is often administered at bedtime. In contrast to the above, the method of the present invention involves the use of a small fraction of such dosages.

The method of the present invention involves the administration of doxepin, amitriptyline, trimipramine, trazodone and mixtures thereof. As noted above, these compounds are well known psychotherapeutic agents which are currently prescribed as antidepressants. Each compound is further readily available commercially. The hydrochloride salt of doxepin is currently marketed by Pfizer Inc. under the tradename Sinequan®. The hydrochloride salt of amitriptyline is currently marketed by Merck & Co., Inc. under the tradename Elavil®. Trimipramine maleate is currently marketed by Wyeth-Ayerst Laboratories under the tradename Surmontil®. The hydrochloride salt of trazodone is currently marketed by Mead Johnson Pharmaceuticals under the tradename Desyrel®.

While the above compounds are commercially available as a hydrochloride salt or, a maleate in the case of trimipramine, it should be understood that the use of other pharmaceutical salts of such compounds are also within the practice of the present invention. Furthermore, although the above compounds are commercially available in various forms, the use of these compounds in other than currently commercially available forms (e.g. injectable solutions, capsules, caplets) is also within the scope of the present invention.

As stated above, dosages of doxepin, amitriptyline, trimipramine or mixtures thereof may vary from about 0.5 to about 20.0 milligrams. Preferably dosages of about 10 milligrams or less are utilized. Most preferably, dosages of about 5 milligrams or less are utilized. With respect to trazodone, dosages of about 0.5 to about 20 milligrams are used. Preferably, dosages of about 15 milligrams or less are used. However, as it is recognized that each individual may react differently to a given dose of the medication used, the dosages recited should be accorded flexibility. Since the point of the present invention is to induce and maintain normal sleep without exposing the patient to residual effect of medication, the lowest effective dosage of the compounds should be utilized whenever possible.

Administration of the compounds should take place within about one hour before bedtime. Again, the onset of the sedative effect will vary with the individual and the dosage prescribed.

The following Examples are offered to illustrate the claimed method and its practice. They should not however be construed in any way as a limitation to the scope of the present invention.

EXAMPLE 1

The patient suffers from onset insomnia (non-chronic). At the time of consultation, she has normal affect with no depression, anxiety or substance overuse. She is prescribed doxepin 10 mg hs. Follow up reveals that the administration of doxepin relieves the onset insomnia and has her sleeping well.

EXAMPLE 2

The patient suffers from onset insomnia (non-chronic). At the time of consultation, he has normal affect with no depression, anxiety or substance overuse. He is prescribed doxepin 20 mg hs. Follow up reveals that the administration of doxepin relieves the onset insomnia and has him sleeping well.

EXAMPLE 3

The patient suffers from onset insomnia (non-chronic) At the time of consultation, he has normal affect with no depression, anxiety or substance overuse. He is prescribed doxepin 5 mg hs. Follow up reveals that the administration of doxepin relieves the onset insomnia and has him sleeping well.

EXAMPLE 4

The patient suffers from onset insomnia (non-chronic). At the time of consultation, he has normal affect with no depression, anxiety or substance overuse. He is prescribed doxepin 2 mg hs. Follow up reveals that the administration of doxepin relieves the onset insomnia and has him sleeping well.

EXAMPLE 5

The patient suffers from onset insomnia (non-chronic). At the time of consultation, she has normal affect with no depression, anxiety or substance overuse. She is prescribed amitriptyline 10 mg hs. Follow up reveals that the administration of amitriptyline relieves the onset insomnia and has her sleeping well.

EXAMPLE 6

The patient suffers from onset insomnia (non-chronic). At the time of consultation, he has normal affect with no depression, anxiety or substance overuse. He is prescribed amitriptyline 20 mg hs. Follow up reveals that the administration of amitriptyline relieves the onset insomnia and has him sleeping well.

EXAMPLE 7

The patient suffers from onset insomnia (non-chronic). At the time of consultation, he has normal affect with no depression, anxiety or substance overuse. He is prescribed amitriptyline 5 mg hs. Follow up reveals that the administration of amitriptyline relieves the onset insomnia and has him sleeping well.

EXAMPLE 8

The patient suffers from onset insomnia (non-chronic). At the time of consultation, she has normal affect with no depression, anxiety or substance overuse. She is prescribed trimipramine 10 mg hs. Follow up reveals that the administration of trimipramine relieves the onset insomnia and has her sleeping well.

EXAMPLE 9

The patient suffers from onset insomnia (non-chronic). At the time of consultation, he has normal affect with no depression, anxiety or substance overuse. He is prescribed trimipramine 20 mg hs. Follow up reveals that the administration of trimipramine relieves the onset insomnia and has him sleeping well.

EXAMPLE 10

The patient suffers from onset insomnia (non-chronic). At the time of consultation, he has normal affect with no depression, anxiety or substance overuse. He is prescribed trimipramine 5 mg hs. Follow up reveals that the administration of trimipramine relieves the onset insomnia and has him sleeping well.

EXAMPLE 11

The patient suffers from onset insomnia (non-chronic). At the time of consultation, she has normal affect with no depression, anxiety or substance overuse. She is prescribed trazodone 20 mg hs. Follow up reveals that the administration of trazodone relieves the onset insomnia and has her sleeping well.

EXAMPLE 12

The patient suffers from onset insomnia (non-chronic). At the time of consultation, he has normal affect with no depression, anxiety or substance overuse. He is prescribed trazodone 10 mg hs. Follow up reveals that the administration of trazodone relieves the onset insomnia and has him sleeping well.

EXAMPLE 13

The patient suffers from onset insomnia (non-chronic). At the time of consultation, he has normal affect with no depression, anxiety or substance overuse. He is prescribed trazodone 15 mg hs. Follow up reveals that the administration of trazodone relieves the onset insomnia and has him sleeping well.

EXAMPLE 14

The patient suffers from maintenance insomnia (non-chronic). At the time of consultation, she has normal affect with no depression, anxiety or substance overuse. She is prescribed doxepin 10 mg hs. Follow up reveals that the administration of doxepin relieves the insomnia and has her sleeping well.

EXAMPLE 15

The patient suffers from maintenance insomnia (non-chronic). At the time of consultation, he has normal affect with no depression, anxiety or substance overuse. He is prescribed doxepin 20 mg hs. Follow up reveals that the administration of doxepin relieves the insomnia and has him sleeping well.

EXAMPLE 16

The patient suffers from maintenance insomnia (non-chronic) At the time of consultation, he has normal affect with no depression, anxiety or substance overuse. He is prescribed doxepin 5 mg hs. Follow up reveals that the administration of doxepin relieves the insomnia and has him sleeping well.

EXAMPLE 17

The patient suffers from maintenance insomnia (non-chronic) At the time of consultation, he has normal affect with no depression, anxiety or substance overuse. He is prescribed doxepin 2 mg hs. Follow up reveals that the administration of doxepin relieves the insomnia and has him sleeping well.

EXAMPLE 18

The patient suffers from maintenance insomnia (non-chronic). At the time of consultation, she has normal affect with no depression, anxiety or substance overuse. She is prescribed amitriptyline 10 mg hs. Follow up reveals that the administration of amitriptyline relieves the insomnia and has her sleeping well.

EXAMPLE 19

The patient suffers from maintenance insomnia (non-chronic). At the time of consultation, he has normal affect with no depression, anxiety or substance overuse. He is prescribed amitriptyline 20 mg hs. Follow up reveals that the administration of amitriptyline relieves the insomnia and has him sleeping well.

EXAMPLE 20

The patient suffers from maintenance insomnia (non-chronic). At the time of consultation, he has normal affect with no depression, anxiety or substance overuse. He is prescribed amitriptyline 5 mg hs. Follow up reveals that the administration of amitriptyline relieves the insomnia and has him sleeping well.

EXAMPLE 21

The patient suffers from maintenance insomnia (non-chronic). At the time of consultation, she has normal affect with no depression, anxiety or substance overuse. She is prescribed trimipramine 10 mg hs. Follow up reveals that the administration of trimipramine relieves the insomnia and has her sleeping well.

EXAMPLE 22

The patient suffers from maintenance insomnia (non-chronic). At the time of consultation, he has normal affect with no depression, anxiety or substance overuse. He is prescribed trimipramine 20 mg hs. Follow up reveals that the administration of trimipramine relieves the insomnia and has him sleeping well.

EXAMPLE 23

The patient suffers from maintenance insomnia (non-chronic). At the time of consultation, he has normal affect with no depression, anxiety or substance overuse. He is prescribed trimipramine 5 mg hs. Follow up reveals that the administration of trimipramine relieves the insomnia and has him sleeping well.

EXAMPLE 24

The patient suffers from maintenance insomnia (non-chronic). At the time of consultation, she has normal affect with no depression, anxiety or substance overuse. She is prescribed trazodone 20 mg hs. Follow up reveals that the administration of trazodone relieves the insomnia and has her sleeping well.

EXAMPLE 25

The patient suffers from maintenance insomnia (non-chronic). At the time of consultation, he has normal affect with no depression, anxiety or substance overuse. He is prescribed trazodone 10 mg hs. Follow up reveals that the administration of trazodone relieves the insomnia and has him sleeping well.

EXAMPLE 26

The patient suffers from maintenance insomnia (non-chronic) At the time of consultation, he has normal affect with no depression, anxiety or substance overuse. He is prescribed trazodone 15 mg hs. Follow up reveals that the administration of trazodone relieves the insomnia and has him sleeping well.

EXAMPLE 27

The patient, a business traveler, suffers from insomnia, possibly due to a desynchronization of circadian rhythms ("jet-lag"). At the time of consultation, she has normal affect with no depression, anxiety or substance overuse. She is prescribed doxepin 10 mg hs. Follow up reveals that the administration of doxepin relieves the insomnia and has her sleeping well.

EXAMPLE 28

The patient, a business traveler, suffers from insomnia, possibly due to a desynchronization of circadian rhythms ("jet-lag"). At the time of consultation, he has normal affect with no depression, anxiety or substance overuse. He is prescribed doxepin 20 mg hs. Follow up reveals that the administration of doxepin relieves the insomnia and has him sleeping well.

EXAMPLE 29

The patient, a business traveler, suffers from insomnia, possibly due to a desynchronization of circadian rhythms ("jet-lag"). At the time of consultation, he has normal affect with no depression, anxiety or substance overuse. He is prescribed doxepin 5 mg hs. Follow up reveals that the administration of doxepin relieves the insomnia and has him sleeping well.

EXAMPLE 30

The patient, a business traveler, suffers from insomnia, possibly due to a desynchronization of circadian rhythms ("jet-lag"). At the time of consultation, he has normal affect with no depression, anxiety or substance overuse. He is prescribed doxepin 2 mg hs. Follow up reveals that the administration of doxepin relieves the insomnia and has him sleeping well.

EXAMPLE 31

The patient, a business traveler, suffers from insomnia, possibly due to a desynchronization of circadian rhythms ("jet-lag"). At the time of consultation, she has normal affect with no depression, anxiety or substance overuse. She is prescribed amitriptyline 10 mg hs. Follow up reveals that the administration of amitriptyline relieves the insomnia and has her sleeping well.

EXAMPLE 32

The patient, a business traveler, suffers from insomnia, possibly due to a desynchronization of circadian rhythms ("jet-lag"). At the time of consultation, he has normal affect with no depression, anxiety or substance overuse. He is prescribed amitriptyline 20 mg hs. Follow up reveals that the administration of amitriptyline relieves the insomnia and has him sleeping well.

EXAMPLE 33

The patient, a business traveler, suffers from insomnia, possibly due to a desynchronization of circadian rhythms ("jet-lag"). At the time of consultation, he has normal affect with no depression, anxiety or substance overuse. He is prescribed amitriptyline 5 mg hs. Follow up reveals that the administration of amitriptyline relieves the insomnia and has him sleeping well.

EXAMPLE 34

The patient, a business traveler, suffers from insomnia, possibly due to a desynchronization of circadian rhythms ("jet-lag"). At the time of consultation, she has normal affect with no depression, anxiety or substance overuse. She is prescribed trimipramine 10 mg hs. Follow up reveals that the administration of trimipramine relieves the insomnia and has her sleeping well.

EXAMPLE 35

The patient, a business traveler, suffers from insomnia, possibly due to a desynchronization of circadian rhythms ("jet-lag"). At the time of consultation, he has normal affect with no depression, anxiety or substance overuse. He is prescribed trimipramine 20 mg hs. Follow up reveals that the administration of trimipramine relieves the insomnia and has him sleeping well.

EXAMPLE 36

The patient, a business traveler, suffers from insomnia, possibly due to a desynchronization of circadian rhythms ("jet-lag"). At the time of consultation, he has normal affect with no depression, anxiety or substance overuse. He is prescribed trimipramine 5 mg hs. Follow up reveals that the administration of trimipramine relieves the insomnia and has him sleeping well.

EXAMPLE 37

The patient, a business traveler, suffers from insomnia, possibly due to a desynchronization of circadian rhythms ("jet-lag"). At the time of consultation, she has normal affect with no depression, anxiety or substance overuse. She is prescribed trazodone 20 mg hs. Follow up reveals that the administration of trazodone relieves the insomnia and has her sleeping well.

EXAMPLE 38

The patient, a business traveler, suffers from insomnia, possibly due to a desynchronization of circadian rhythms ("jet-lag"). At the time of consultation, he has normal affect with no depression, anxiety or substance overuse. He is prescribed trazodone 20 mg hs. Follow up reveals that the administration of trazodone relieves the insomnia and has him sleeping well.

EXAMPLE 39

The patient, a business traveler, suffers from insomnia, possibly due to a desynchronization of circadian rhythms ("jet-lag"). At the time of consultation, he has normal affect with no depression, anxiety or substance overuse. He is prescribed trazodone 15 mg hs. Follow up reveals that the administration of trazodone relieves the insomnia and has him sleeping well.

What is claimed is:

1. A method for the treatment of a patient suffering from non-chronic insomnia of from one night to about three weeks in duration comprising administering to said patient a compound selected from the group consisting of the pharmaceutically acceptable forms of doxepin, amitriptyline, trimipramine, trazodone and mixtures thereof in a daily dosage ranging from about 0.5 to about 20 milligrams.

2. The method of claim 1 wherein the pharmaceutically acceptable form of doxepin, amitriptyline, trazodone and mixtures thereof are the hydrochloride salts thereof and the pharmaceutically acceptable form of trimipramine is the maleate salt.

3. The method of claim 1 wherein the dosage of doxepin, amitriptyline, trimipramine and mixtures thereof is about 10 milligrams or less.

4. The method of claim 1 wherein the dosage is about 5 milligrams or less.

5. The method of claim 1 wherein the compound is doxepin hydrochloride.

6. The method of claim 5 wherein the dosage is about 10 milligrams or less.

7. The method of claim 5 wherein the dosage is about 5 milligrams or less.

8. The method of claim 1 wherein the compound is amitriptyline.

9. The method of claim 8 wherein the dosage is about 10 milligrams or less.

10. The method of claim 8 wherein the dosage is about 5 milligrams or less.

11. The method of claim 1 wherein the compound is trimipramine.

12. The method of claim 11 wherein the dosage is about 10 milligrams or less.

13. The method of claim 11 wherein the dosage is about 5 milligrams or less.

14. The method of claim 1 wherein the compound is trazodone.

15. The method of claim 14 wherein the dosage of trazodone ranges from about 5 to about 15 milligrams.

16. The method of claim 1 wherein non-chronic insomnia is onset insomnia.

17. The method of claim 16 wherein the dosage of doxepin, amitriptyline, trimipramine and mixtures thereof is about 10 milligrams or less.

18. The method of claim 17 wherein the dosage is about 5 milligrams or less.

19. The method of claim 16 wherein the compound is doxepin hydrochloride.

20. The method of claim 19 wherein the dosage is about 10 milligrams or less.

21. The method of claim 19 wherein the dosage is about 5 milligrams or less.

22. The method of claim 16 wherein the dosage of trazodone is about 15 milligrams or less.

23. The method of claim 22 wherein the dosage is about 10 milligrams or less.

24. The method of claim 1 wherein non-chronic insomnia is maintenance insomnia.

25. The method of claim 24 wherein the dosage of doxepin, amitriptyline, trimipramine and mixtures thereof is about 10 milligrams or less.

26. The method of claim 25 wherein the dosage is about 5 milligrams or less.

27. The method of claim 25 wherein the compound is doxepin hydrochloride.

28. The method of claim 27 wherein the dosage is about 10 milligrams or less.

29. The method of claim 27 wherein the dosage is about 5 milligrams or less.

30. The method of claim 24 wherein the dosage of trazodone is about 15 milligrams or less.

31. The method of claim 30 wherein the dosage is about 10 milligrams or less.

* * * * *